US008205994B1

(12) United States Patent
Chapman

(10) Patent No.: US 8,205,994 B1
(45) Date of Patent: Jun. 26, 2012

(54) MINIMUM RETROREFLECTIVITY COMPLIANCE SYSTEM, METHOD AND ASSEMBLY

(75) Inventor: Scott N. Chapman, Pickerington, OH (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 13/098,618

(22) Filed: May 2, 2011

(51) Int. Cl.
*G02B 5/124* (2006.01)

(52) U.S. Cl. ......... 359/530; 359/532; 359/896; 356/445

(58) Field of Classification Search .......... 359/529–441; 356/445; 382/104, 165
See application file for complete search history.

(56) References Cited

U.S. PATENT DOCUMENTS 6,674,878 B2 * 1/2004 Retterath et al. .............. 382/104
2009/0252376 A1 * 10/2009 Retterath et al. .............. 382/104

* cited by examiner

*Primary Examiner* — James Phan
(74) *Attorney, Agent, or Firm* — Avery Dennison Corporation

(57) ABSTRACT

A system, method and assembly for performing traffic sign inspections is provided. In one embodiment, the assembly includes a first plurality of sheetings that each have a combination of retroreflectivity and color that is different from the combination of retroreflectivity and color of each of the other first plurality of sheetings; a first clamp and second clamp for clamping one of said first plurality of sheetings to a traffic sign; a first handheld light source; and a first enclosure for removably housing the first plurality of sheetings, said first and second clamps, and said first handheld light source. The assembly may further include a second enclosure for removably housing a second plurality of sheetings that each has a combination of retroreflectivity and color that is different from the combination of retroreflectivity and color of each of the other second plurality of sheetings.

6 Claims, 4 Drawing Sheets

200

220
210a
210b 210c 210d 210e
210f 240a
200
240b
235a
210g
235b
210h 210i 210j 210k 210l

MINIMUM RETROREFLECTIVITY COMPLIANCE SYSTEM, METHOD AND ASSEMBLY

CROSS-REFERENCE TO RELATED APPLICATION(S)

None.

FIELD OF THE INVENTION

The present invention is directed to testing of retroreflectivity of traffic signs and, more particularly, to a system, method and assembly for determining compliance of the retroreflectivity of traffic signs with a minimum retroreflectivity requirement.

BACKGROUND OF THE INVENTION

While only one-quarter of all travel occurs at night, about half of the traffic fatalities occur during nighttime hours. To address this disparity and promote highway safety, the Federal Highway Administration (FHWA) has adopted traffic sign retroreflectivity requirements. Regulations contained in the Manual of Uniform Traffic Control Devices (MUTCD) include a standard for minimum levels of retroreflectivity that must be maintained for traffic signs. The regulation applies to most regulatory, warning, street name, ground-mounted and overhead guide signs, whether permanent, temporary or portable, on all public roads and private property where the public is invited to travel.

In order to maintain traffic sign retroreflectivity at or above the minimum levels, it is necessary to have a device with which to measure the retroreflectivity levels of the sheeting, or possess a visual reference standard that can be compared against the traffic sign. As one method of determining that signs are at or above the minimum levels, the FHWA recommends that all agencies conduct nighttime visual assessments of individual traffic signs within their jurisdiction. The process requires a sign inspector to view a sign at a known retroreflective level which is at the minimum level defined by the standard to establish the evaluation threshold for that night's inspection activities. Agencies typically may find such signs by looking through their inventory of old or discarded signs (if available). However, without equipment to measure the retroreflectivity of these old or discarded signs, the agency does not know if their discarded sign is an accurate representation of the minimum standard. Most agencies do not possess devices to measure retroreflectivity. Portable retroreflectometers typically are priced beyond the maintenance budgets of many city, county, village and townships that are responsible for maintaining the signs. Further, the devices themselves are not well suited to the rigors of being constantly used in the field by maintenance crews, thereby requiring ongoing maintenance and periodic calibration to accurately measure retroreflectivity.

When nighttime visual sign inspections result in the identification of signs which may have marginal retroreflectivity (i.e., the signs are determined by the inspector to not clearly be above the minimum retroreflectivity), an agency requires the means to determine if the sign is above, or below the minimum standard. If an agency possesses a portable retroreflectometer, a measurement can be conducted, and a decision regarding the continued effectiveness (and use) of the sign can be made. As an alternate procedure, an inspector may attach smaller panels cut from older signs that are at the minimum retroreflectivity levels to the sign in question, and conduct a comparative review under retroreflected light. However, without a retroreflectometer to measure sign retroreflectivity, the inspector cannot be certain that the smaller panel is at the required minimum retroreflectivity level or is an accurate visual representation of the minimum standard.

Thus, it would be desirable to provide a plurality of retroreflective sheeting, having various colors and retroreflectivity levels that are known and/or certified to be at the minimum retroreflectivities required by the MUTCD standard. These and other advantages may be provided by one or more embodiments of the present invention.

BRIEF SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

The present invention comprises a system, method and assembly for performing traffic sign inspections. In one embodiment, the assembly includes a first plurality of sheetings that each have a combination of retroreflectivity and color that is different from the combination of retroreflectivity and color of each of the other first plurality of sheetings; a first clamp and second clamp for clamping one of said first plurality of sheetings to a traffic sign; a first handheld light source; and a first enclosure for removably housing the first plurality of sheetings, said first and second clamp, and said first handheld light source. The assembly may further include a second enclosure for removably housing a second plurality of sheetings that each has a combination of retroreflectivity and color that is different from the combination of retroreflectivity and color of each of the other second plurality of sheetings.

In a further exemplary embodiment of the presently described invention, an assembly for performing traffic sign inspections is provided and includes a first enclosure for removably housing a first plurality of sheetings. The sheetings or calibrated signs including a first white sheeting having a retroreflectivity level of at least 35 cd/lx/$m^2$; a second white sheeting having a retroreflectivity level of at least 50 cd/lx/$m^2$; a third white sheeting having a retroreflectivity level of at least 120 cd/lx/$m^2$; a fourth white sheeting having a retroreflectivity level of at least 250 cd/lx/$m^2$; a first green sheeting having a retroreflectivity level of at least 7 cd/lx/$m^2$; a second green sheeting having a retroreflectivity level of at least 15 cd/lx/$m^2$; a third green sheeting having a retroreflectivity level of at least 25 cd/lx/$m^2$; a first yellow sheeting having a retroreflectivity level of at least 50 cd/lx/$m^2$; a second yellow sheeting having a retroreflectivity level of at least 75 cd/lx/$m^2$; a first orange sheeting having a retroreflectivity level of at least 50 cd/lx/$m^2$; a second orange sheeting having a retroreflectivity level of at least 75 cd/lx/$m^2$; a first red sheeting having a retroreflectivity level of at least 7 cd/lx/$m^2$; an attachment device for attaching one of said first plurality of sheetings to a traffic sign; and a first handheld light source.

In a still further exemplary embodiment of the presently described invention, a method of determining compliance of a sign with a minimum retroreflectivity, is described and includes the steps of initially selecting a color and retroreflectivity of the sign to be tested, then selecting a comparison panel from a plurality of comparison panels. Next, the selected comparison panel is attached to the sign. The sign and comparison panel is illuminated with a light source. The retroreflectivity of the illuminated sign and the retroreflectivity of the illuminated comparison panel are compared and then it is determined whether the retroreflectivity of the illuminated sign is less than retroreflectivity of the illuminated comparison panel. Finally, scheduling the sign for replacement if the retroreflectivity of the sign is less than the retroreflectivity of the comparison panel.

In a still further exemplary embodiment of the presently described invention, an assembly for performing traffic sign inspections is provided and includes: a first plurality of sheetings with each of said first plurality of sheetings having a combination of retroreflectivity and color that is different from the combination of retroreflectivity and color of each of the other first plurality of sheetings, a first clamp and second clamp for clamping one of the first plurality of sheetings to a traffic sign; a first handheld light source, and a first enclosure for removably housing the first plurality of sheetings, and the first and second clamp, and first handheld light source.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

The apparatuses and methods disclosed in this document are described in detail by way of examples and with reference to the figures. Unless otherwise specified, like numbers in the figures indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be, and should not be, construed as mandatory or limiting unless specifically designated as such. Selected examples of apparatuses and methods are hereinafter disclosed and described in detail with reference made to FIGURES.

Embodiments of the present invention provide visual sheetings having a retroreflectivity known to be equal to (or within a predetermined tolerance of) the minimum levels defined by the MUTCD. The sheetings may be used to establish viewing threshold and/or be compared to "marginal" traffic signs to determine whether replacement of the traffic sign is warranted. Embodiments may include one or more light sources suitable for comparing sheetings with traffic signs at nighttime or daytime and one or more clamps for attaching a sheeting to a traffic sign.

Figure 1:
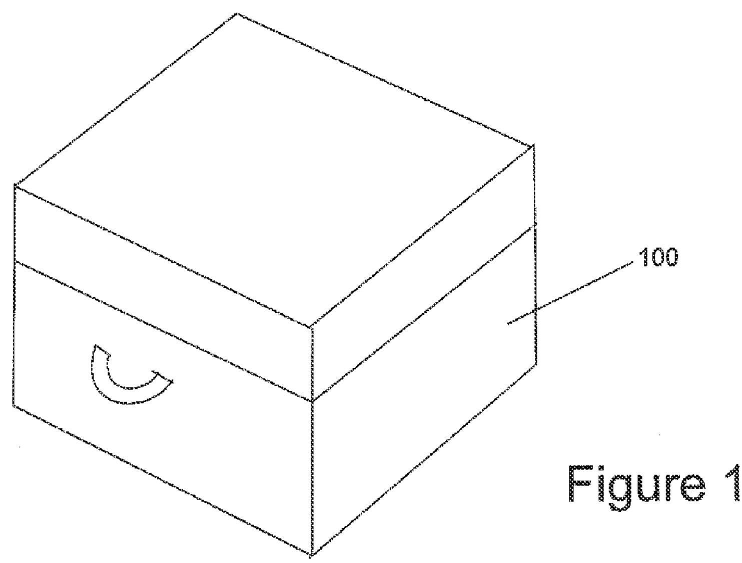
FIG. 1 depicts an enclosure for carrying a plurality of calibrated signs in accordance with an example embodiment of the present invention.
Figure 2:
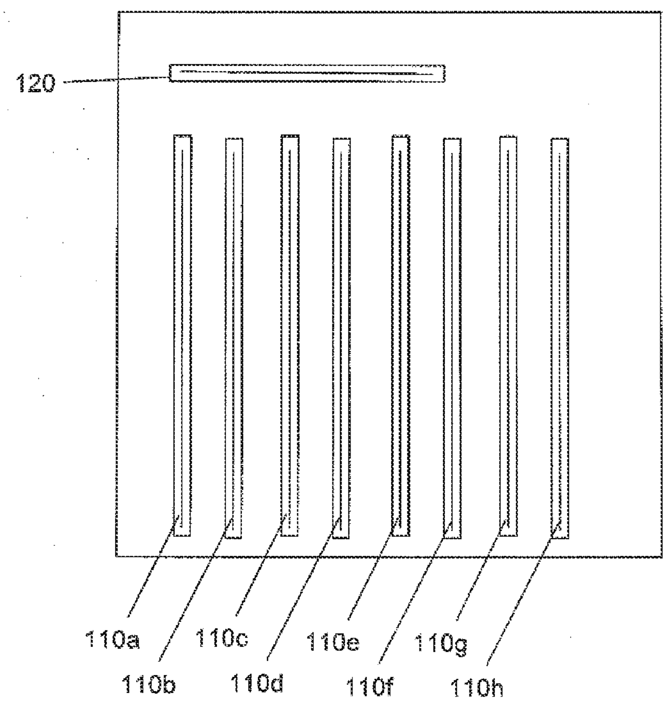
FIG. 2 depicts the inside of the enclosure of FIG. 1 in accordance with an example embodiment of the present invention.

One example embodiment of the present invention comprises an enclosure that contains all of the necessary tools for a sign Inspector to establish the evaluation threshold for nighttime sign inspections and to conduct individual sign inspections of marginal signs. More specifically, this example embodiment includes eight calibrated signs and twelve comparison panels in color combinations identified by Table 2A-3 of the MUTCD and that are manufactured using T-5500, encapsulated beaded material, retroreflective sheeting, available from Avery Dennison Corporation, Niles, Ill., with retroreflectivity levels engineered and certified to comply with the minimum levels defined by the standard (the MUTCD). As illustrated in FIGS. 1 and 2 a watertight sign enclosure 100 may be used to house the first plurality of sheetings that comprise the eight calibrated signs 110*a-h*. Table I below identifies the calibrated signs forming part of this example embodiment.

TABLE 1

Calibrated Signs

| FIG. 2 label | Color Combination | Retroreflectivities | Sheeting Type |
|---|---|---|---|
| 110a | White on Green | White 250; Green 25 | Beaded |
| 110b | White on Green | White 120, Green 15 | Beaded |
| 110c | Black on Yellow | Yellow 50 | Beaded |
| 110d | Black on Yellow | Yellow 75 | Beaded |
| 110e | Black on Orange | Orange 50 | Beaded |
| 110f | Black on Orange | Orange 75 | Beaded |
| 110g | White on Red | White 35, Red 7 | Beaded |
| 110h | Black on White | White 50 | Beaded |

TABLE 2

Calibrated Signs—Range

| Calibrated Panel | Color | | Coefficient of Retroreflection ($R_A$) d/lx/m² cat O.A. 0.2° and E.A. −4.0° | |
|---|---|---|---|---|
| No. | Background | Legend | Minimum | Maximum |
| 110a | Green | | 25 | 33 |
| | | White | 250 | 285 |
| 110b | Green | | 15 | 22 |
| | | White | 120 | 145 |
| 110c | Yellow | | 50 | 60 |
| | | Black | n/a | n/a |

TABLE 2-continued

Calibrated Signs—Range

| Calibrated Panel | Color | | Coefficient of Retroreflection ($R_A$) d/lx/m$^2$ cat O.A. 0.2° and E.A. −4.0° | |
|---|---|---|---|---|
| No. | Background | Legend | Minimum | Maximum |
| 110d | Orange | | 50 | 60 |
| | | Black | n/a | n/a |
| 110e | Yellow | | 75 | 90 |
| | | Black | n/a | n/a |
| 110f | Orange | | 75 | 90 |
| | | Black | n/a | n/a |
| 110g | Red | | 7 | 12 |
| | | White | 35 | 45 |
| 110h | White | | 50 | 60 |
| | | Black | n/a | n/a |

TABLE 3

Calibrated Signs—Comparison

| Comparison Panel | | Coefficient of Retroreflection ($R_A$) cd/lx/m$^2$ at O.A. 0.2°and E.A. −4.0° | |
|---|---|---|---|
| No. | Color | Minimum | Maximum |
| 1 | Green | 7 | 12 |
| 2 | Green | 15 | 22 |
| 3 | Green | 25 | 33 |
| 4 | White | 250 | 285 |
| 5 | White | 120 | 145 |
| 6 | Yellow | 50 | 60 |
| 7 | Orange | 50 | 60 |
| 8 | Yellow | 75 | 90 |
| 9 | Orange | 75 | 90 |
| 10 | White | 35 | 45 |
| 11 | Red | 7 | 12 |
| 12 | White | 50 | 60 |

Reflectivity in the above table and elsewhere herein is designated in units of cd/lx/m$^2$ (candela per lux per square meter) and measured at an observation angle of 0.2° and an entrance angle of −4.0° (as defined by the MUTCD). In this embodiment, the calibrated signs 110*a-h* are twenty four inch squares (although other shapes and sizes may be used) and may be fabricated using retroreflective sheeting that has no visual orientation sensitivity (e.g., T-5500 offered by Avery Dennison®). Each of the calibrated signs 110 is removably housed in a separate compartment of the enclosure 100, whose interior (shown in FIG. 2) may be formed of foam, plastic, and/or other suitable material. The enclosure 100 may also include a compartment 120 for receiving a manual or guide book for using the calibrated signs. While the use of beaded film has been described in the table above, it should be understood that prismatic films may also be suitable for use in connection with this invention or alternatively, a combination of beaded and prismatic films.

The films used in connection with this invention are also preferably position or orientation insensitive. Where a prismatic film is used, the prismatic film preferably will have a tiled arrangement of the sheeting. That is, discrete tiles are arranged at orientations of 0°, 90°, 180° and 270° forming a tiled pattern. In this manner, regardless of how the sheeting is applied to a surface, it will maintain substantially the same level of performance.

Calibrated signs 110*a-h* are attached to a post, fence or other mounting fixture at regulation height (e.g., five feet) and, using an inspection vehicle with properly aimed and adjusted headlights, the inspector views the calibrated signs 110*a-h* at nighttime from the vehicle at typical viewing distances for traffic signs. In some instances, the inspector may view the calibrated signs 110*a-h* from the vehicle while the vehicle is moving. The visual brightness of the signs 110*a-h* from this procedure is used to establish the viewing threshold of the night's inspection activities. Different locations, weather, or nighttime ambient lighting (e.g., full moon versus new or no moon) may vary the perceived retroreflectivity of the signs. Thus, prior to beginning the night's inspections, the inspector may view the calibrated signs 110*a-h* in order to gauge (or set) the minimum retroreflectivity that inspector must perceive for each traffic sign (for a sign to warrant no further evaluation). After viewing, all of the calibrated signs 110*a-h* may be stored in the enclosure 100 to provide protection against physical damage, and to protect against other environmental exposure which could hasten retroreflective deterioration over time. Alternatively, the calibrated signs 110-*a-h* may be placed securely in a maintenance location for further use.

Ideally, the calibrated signs 110*a-h* should be replaced approximately every two years or earlier when the signs have been scratched or damaged and performance may have been compromised.

The inspector may travel to the traffic signs in the designated area to thereby identify traffic signs whose retroreflectivity is marginal, which means that the perceived retroreflectivity is below a predetermined retroreflectivity threshold. The predetermined retroreflectivity threshold will be determined by the calibrated signs 110*a-h* viewed by the inspector (as discussed above). The inspector may inspect the signs as the inspector drives by the signs in the moving inspection vehicle or may stop the vehicle in front of the traffic sign to perform the visual inspection. The inspector may record each traffic sign determined to have marginal retroreflectivity so additional evaluation may be performed later or immediately.

Figure 3:
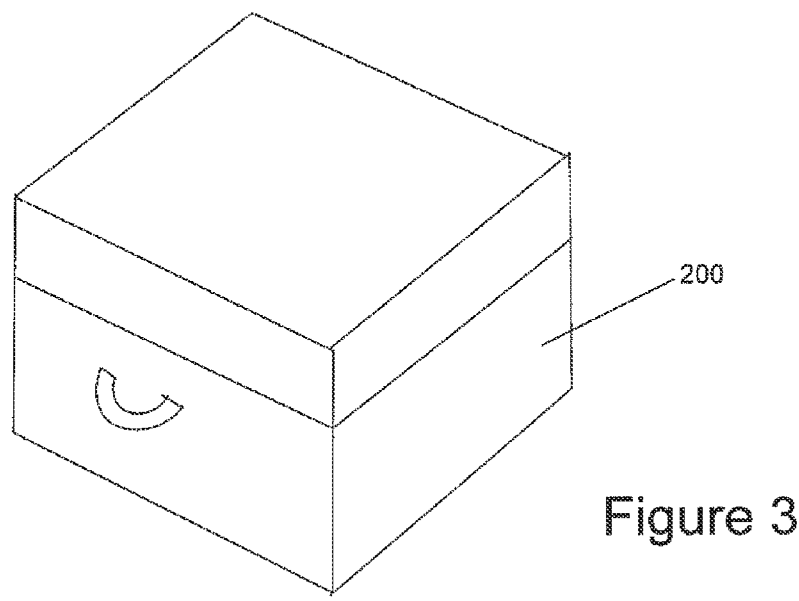
FIG. 3 depicts an enclosure for carrying a plurality of comparison panels, one or more light sources, and one or more clamps in accordance with an example embodiment of the present invention.
Figure 4:
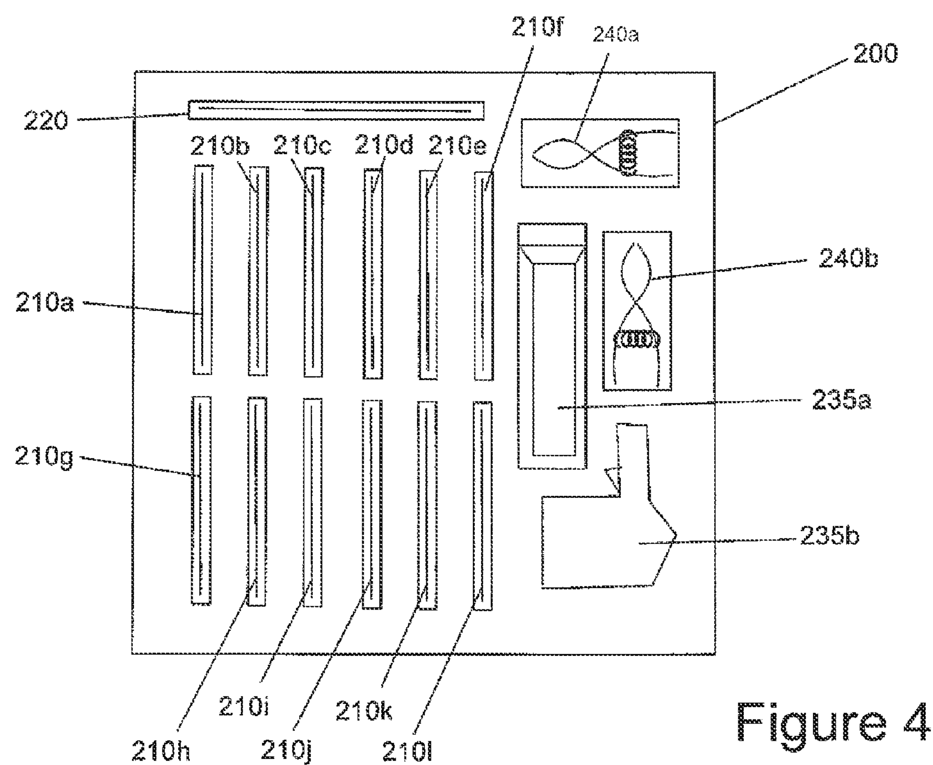
FIG. 4 depicts the inside of the enclosure of FIG. 2 in accordance with an example embodiment of the present invention.

When the inspector determines that a traffic sign has marginal retroreflectivity (from the procedure discussed above), the inspector may need or wish to perform additional evaluation of the traffic sign. Referring to FIGS. 3 AND 4, as discussed above, this example embodiment of the present invention may include a control panel assembly that comprises two light sources 235*a-b*, two clamps 240*a-b*, a manual and guide 220, and a plurality of sheetings (or control panels) 210*a-l* housed in the watertight panel enclosure 200. Other embodiments may include fewer components (such as only one light source), different or additional components.

First, the sign marked for additional evaluation is cleaned according to the recommendations of the retroreflective sheeting manufacturer. Next, the inspector selects and retrieves one (or sometimes two) control panels 210 that matches the traffic sign (i.e., size and background color) being inspected. In some instances, the inspector may not visually be able to determine the retroreflectivity of a sign. However, the inspector may determine the retroreflectivity of the sign by observing other characteristics of the sign in view of Table 2A-3 of the MUTCD. For example, a yellow or orange sign with text and fine and bold symbols measuring at least forty eight inches is required to have a retroreflectivity of at least 50 cd/lx/m$^2$ while a yellow or orange sign having text and fine symbols measuring less than forty-eight inches is required to have a retroreflectivity of at least 75 cd/lx/m$^2$ (as dictated by Table 2A-3 of the MUTCD). Table 2A-3 of the MUTCD is hereby incorporated by reference. Like the calibrated signs 110, the control panels 210 are produced using retroreflective sheeting with retroreflectivity levels engineered and certified to comply with the minimum standard for the particular traffic sign category.

Table 4 below identifies the comparison panels forming part of this example embodiment.

TABLE 4

| Comparison Panels | | |
|---|---|---|
| Color | Retroreflectivity | Sheeting Type |
| Green | 7 | Beaded |
| Green | 15 | Beaded |
| Green | 25 | Beaded |
| White | 35 | Beaded |
| White | 50 | Beaded |
| White | 120 | Beaded |
| White | 250 | Beaded |
| Yellow | 50 | Beaded |
| Yellow | 75 | Beaded |
| Orange | 50 | Beaded |
| Orange | 75 | Beaded |
| Red | 7 | Beaded |

Figure 5:
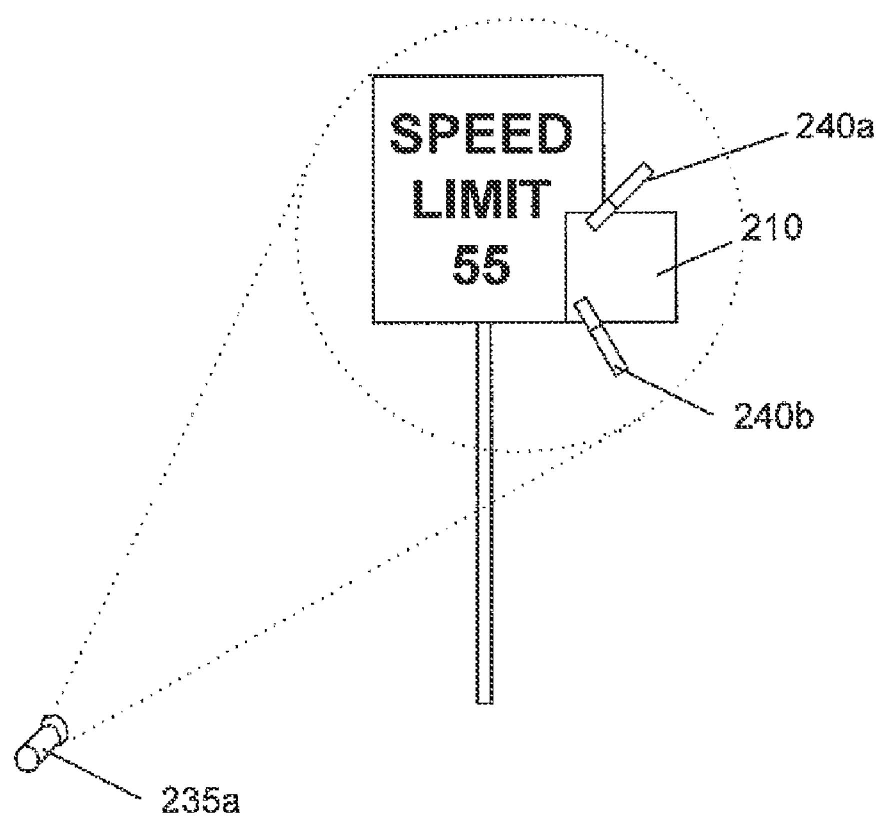
FIG. 5 depicts illumination of a comparison panel attached to a traffic sign in accordance with an example embodiment of the present invention.

The selected comparison panel 210 is then clamped to the traffic sign using the two sign clamps 240*a* and 240*b* as illustrated in FIG. 5. In this embodiment, the comparison panels are six inch squares although other shapes and sizes may be used. In this embodiment, the comparison panels 210 are fabricated using retroreflective sheeting that has no visual orientation sensitivity (e.g., T-5500 offered by Avery Dennison®). Consequently, the panels 210 may be attached in any orientation to signs of any shape including: square, rectangle, octagon, circle, or diamond. After the selected comparison panel 210 is clamped to the sign, the inspector stands a minimum of twenty-five feet from the sign and, while holding the LED flashlight 235*a* at approximately eye level, radiates the comparison panel 210 and sign. The inspector views the radiated traffic sign and comparison panel 210 to compare the retroreflectivity of each. If the visual appearance reveals the sign to be brighter than the comparison panel 210, the sign is determined (judged by the inspector) to be above the minimum standard, and may remain in service. If, however, the comparison panel 210 is determined (e.g., judged) to be brighter than the traffic sign, then the inspector may mark the sign to be scheduled for replacement. The LED flashlight will be more visible at times other than bright sunlight conditions. The LED has a output of at least about 20 lumens.

Figure 6:
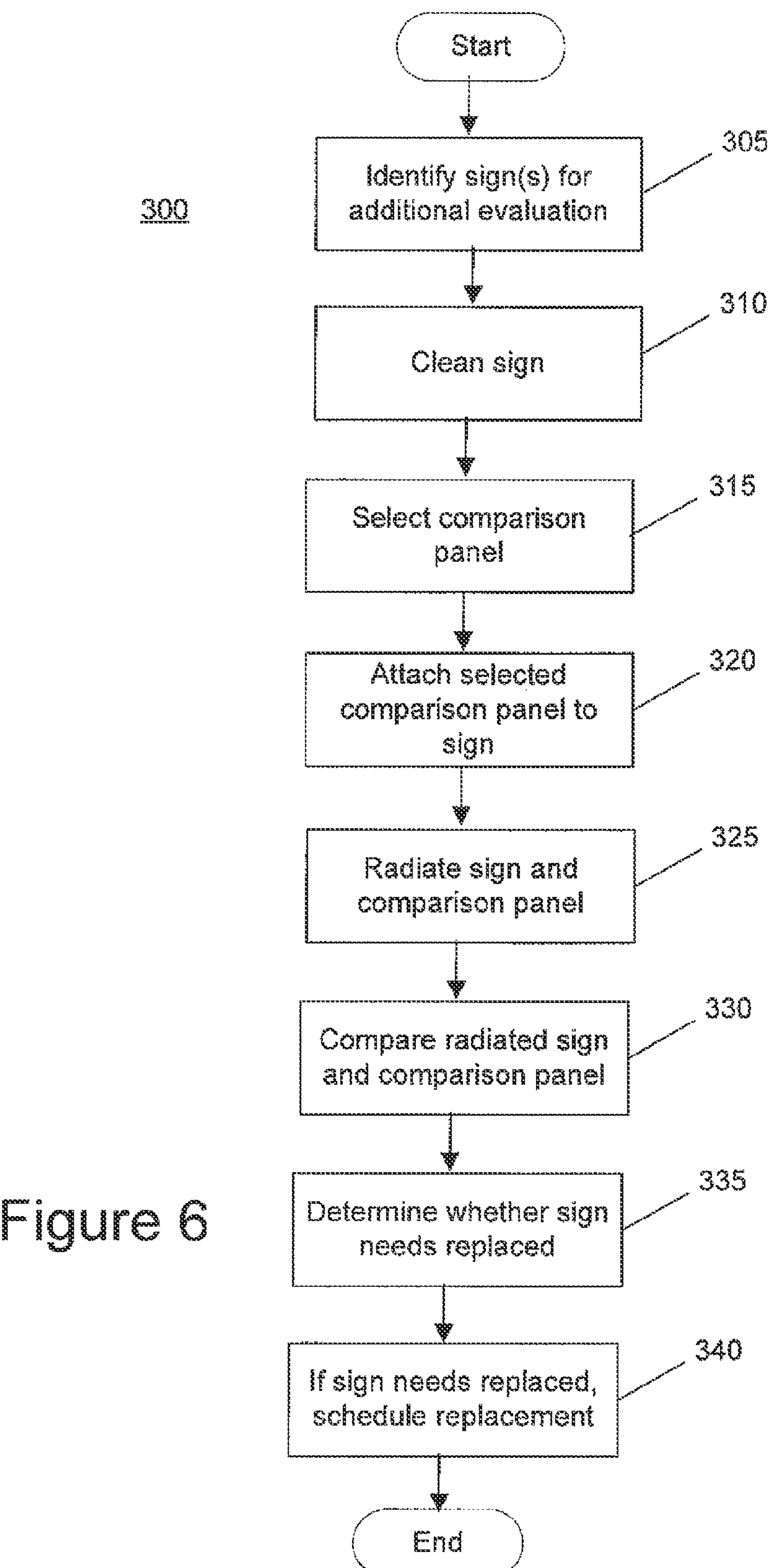
FIG. 6 illustrates a method for testing compliance with minimum retroreflectivity standards according to an example embodiment of the present invention.

FIG. 6 illustrates a method 300 for testing compliance with minimum retroreflectivity standards according to an example embodiment of the present invention. At 305 the sign(s) determined to require additional evaluation are identified such as by using the calibrated signs according to the method described above or another method. At 310 the sign to be tested is cleaned in accordance with manufacturer recommendations. At 315 a comparison panel is selected (from the plurality of comparison panels) to match the characteristics (color and retroreflectivity of the background of the sign) of the sign being tested. At 320 the selected comparison panel 210 is attached to the sign such as by using two or more clamps 240. At 325 the sign and comparison panel 210 are radiated (illuminated) such as by using an LED flashlight 235*a*. At 330 the inspector views and compares the retroreflectivity of the radiated sign and comparison panel 210. At 335 the inspector determines, based on the comparison, whether the sign is less bright than the comparison panel 210 and therefore needs replaced. At 340, if the sign needs replaced, the inspector may schedule replacement and/or record the determination that the sign needs replacement (including information identifying the sign and/or its location).

Nighttime sign inspections have two problems for agencies. First, nighttime inspections are inherently more dangerous with the loss of visual clues that exist during daylight hours. Further, motorists are less attentive due to fatigue, creating a dangerous work environment for inspectors. In addition, agencies often find themselves in situations where they are required to pay overtime labor rates for nighttime inspectors. Because of these factors, it may be desirable to an agency to conduct daytime secondary inspections for signs judged marginal during the nighttime review.

Daytime secondary inspections may be conducted using the comparison panels in a manner similar to the manner described for nighttime inspections. However, instead of using the LED flashlight 235*a*, the inspector may use a larger 1,000,000 candlepower light source 235*b* (or at least a 500,000 candlepower light source) also enclosed in the panel enclosure 200 to achieve sufficient luminance to create, view, and compare retroreflective performances of the panel 210 and sign in daylight. If the visual inspection reveals the sign to be brighter than the comparison panel 210, the sign is judged to be above the minimum standard, and may remain in service. If the comparison panel 210 is determined to be brighter than the traffic sign, then the sign may marked (and/or scheduled) for replacement.

Enclosures 100 and 200 of both the calibrated signs 110 and the comparison panels 210 may have slots in a foam bedding (or plastic) to hold each panel 210 (or sign 110) in a position in which the panel 210 (or sign 110) does not contact other panels 210 (or signs 110) as is illustrated in the figures. Alternatively, the signs may be stacked horizontally in an area sized and configured for the signs and may have protective slip sheets between each of the signs. Each enclosure may comprise a heavy-duty, durable, watertight case that will withstand the rigors of transport ln the back of a maintenance truck.

In addition, the enclosures 100 and 200 may each also have a compartment 110 and 210 (e.g., foam compartment) for holding a manual of instructions that details the procedure(s) to be used by the inspector. In addition, the panel enclosure may have a compartment (e.g., foam compartment) sized and shaped to receive each of the two flashlights 235 and clamps 240 to be used by the inspector. The comparison panels 210 and calibrated signs 110 may include labels or other indicia on the back side (or front side) to indicate the retroreflectivity of the panel or sign. Alternately or additionally, each slot that holds a panel 210 or calibrated sign 110 may be labeled with the color (or color combination) and/or retroreflectivity.

The marking of traffic signs to be additionally evaluated and/or replaced may be performed by storing data in computer such as a database stored on a portable computer of the inspection vehicle or a database stored remotely that is accessed wirelessly via a portable computing device. In addition or alternately, the signs may be physically marked such as with reflective tape.

While the tables above reference various retroreflectivities and colors, other embodiments may include additional (or different) sheetings of other sizes, colors, retroreflectivities, color combinations, sheeting types (beading, prismatic), and/or other characteristics. In addition, while the retroreflectivity of the comparison panels and calibrated signs ideally would be exactly at the minimum defined by the MUTCD standard (identified in the tables above), in practice measurement (and manufacturing) tolerances may result in slight variations to such minimums that may not be generally perceivable by human observation.

While the above embodiment includes include a control panel assembly and a calibrated sign assembly, other embodiments may include only the control panel assembly or only the calibrated sign assembly.

Each of the two clamps may be spring clamps that are urged closed by the spring and include rubber or other non-slip material on the clamping end and/or the handles. While the above embodiment includes two clamps, other embodiments may include one clamp, or three or more clamps.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. An assembly for performing traffic sign inspections, comprising:

a first plurality of sheetings;

wherein each of said first plurality of sheetings has a combination of retroreflectivity and color that is different from the combination of retroreflectivity and color of each of the other first plurality of sheetings;

a first clamp and second clamp for clamping one of said first plurality of sheetings to a traffic sign;

a first handheld light source; and a first enclosure for removably housing the first plurality of sheetings, said first and second clamps, and said first handheld light source.

2. The assembly of claim 1, wherein said first plurality of sheetings comprises:

a first white sheeting having a retroreflectivity level of at least 35 cd/lx/$m^2$;

a second white sheeting having a retroreflectivity level of at least 50 cd/lx/$m^2$;

a third white sheeting having a retroreflectivity level of at least 120 cd/lx/$m^2$;

a fourth white sheeting having a retroreflectivity level of at least 250 cd/lx/$m^2$;

a first green sheeting having a retroreflectivity level of at least 7 cd/lx/$m^2$;

a second green sheeting having a retroreflectivity level of at least 15 cd/lx/$m^2$;

a third green sheeting having a retroreflectivity level of at least 25 cd/lx/$m^2$;

a first yellow sheeting having a retroreflectivity level of at least 50 cd/lx/$m^2$;

a second yellow sheeting having a retroreflectivity level of at least 75 cd/lx/$m^2$;

a first orange sheeting having a retroreflectivity level of at least 50 cd/lx/$m^2$;

a second orange sheeting having a retroreflectivity level of at least 75 cd/lx/$m^2$; and a first red sheeting having a retroreflectivity level of at least 7 cd/lx/$m^2$.

3. The assembly of claim 1, further comprising a second handheld light source having a light output of at least 500,000 candlepower lights.

4. The assembly of claim 1, wherein said first enclosure comprises:

a first compartment sized and shaped to receive said first handheld light source;

a second compartment sized and shaped to receive said first clamp; and a third compartment sized and shaped to receive said second clamp.

5. The assembly of claim 1, further comprising a second enclosure for removably housing a second plurality of sheetings;

wherein each of the second plurality of sheetings has a combination of retroreflectivity and color that is different from the combination of retroreflectivity and color of each of the other second plurality of sheetings.

6. The assembly of claim 5, wherein said second plurality of sheetings comprises:

a first sheeting with white having a retroreflectivity level of at least 250 cd/lx/$m^2$ and green having a retroreflectivity level of at least 25 cd/lx/$m^2$;

a second sheeting with white having a retroreflectivity level of at least 120 cd/lx/$m^2$ and green background having a retroreflectivity level of at least 15 cd/lx/$m^2$;

a third sheeting that includes yellow having a retroreflectivity level of at least 50 cd/lx/$m^2$;

a fourth sheeting that includes yellow having a retroreflectivity level of at least 75 cd/lx/$m^2$;

a fifth sheeting that includes orange having a retroreflectivity level of at least 50 cd/lx/$m^2$;

a sixth sheeting that includes orange having a retroreflectivity level of at least 75 cd/lx/$m^2$;

a seventh sheeting with white having a retroreflectivity level of at least 35 cd/lx/$m^2$ and red having a retroreflectivity level of at least 7 cd/lx/$m^2$; and an eighth sheeting with white having a retroreflectivity level of at least 50 cd/lx/$m^2$.

* * * * *